United States Patent [19]

Tesini

[11] Patent Number: 4,624,640
[45] Date of Patent: Nov. 25, 1986

[54] WAFER FOR A DENTAL IMPRESSION FOR IDENTIFICATION PURPOSES

[76] Inventor: David A. Tesini, 29 Knowles Ave., Auburn, Mass. 01501

[21] Appl. No.: 668,737

[22] Filed: Nov. 6, 1984

[51] Int. Cl.⁴ .............................................. A61C 9/00
[52] U.S. Cl. ...................................................... 433/71
[58] Field of Search .................................. 433/71, 229

[56] References Cited

U.S. PATENT DOCUMENTS

| | | | |
|---|---|---|---|
| 2,183,624 | 12/1939 | Scwartz | 433/71 |
| 4,482,321 | 11/1984 | Tabor et al. | 433/71 |
| 4,508,156 | 4/1985 | Banks et al. | 433/71 |

*Primary Examiner*—Robert Peshock
*Attorney, Agent, or Firm*—Robert E. Ross

[57] ABSTRACT

A method and article for providing identification means, comprising taking an impression of teeth with a wax wafer of special configuration such that the wafer receives an impression which gives the size and shape of each tooth from the occusal surface to the gum line, and also provides information on tooth position and jaw relationship, to provide maximum information for identification. The wafer with the impression is then stored for use in case of need, preferably in a container which is sealed so that tampering with the contents can be detected.

5 Claims, 6 Drawing Figures

WAFER FOR A DENTAL IMPRESSION FOR IDENTIFICATION PURPOSES

BACKGROUND OF THE INVENTION

In providing means for identification of missing persons, photographs, fingerprints and dental chartings are commonly used. However, in the identification of a human body in which substantial decomposition has occurred, the use of fingerprints is often not possible, and in such cases dental chartings, if available, are often used.

Forensic odontology, the branch of dentistry which is concerned with identification of corpses by dental and oral characteristics often plays a major role in the identification of missing persons and victims of crime and accidents.

However, if the victim has no dental record, identification by such means is obviously impossible. This is often the case with young children that are missing. A very large percentage of children of pre-school age have never visited a dentist, and a large percentage of those who have visited a dentist merely have an examination for tooth decay or other dental purposes. This record is seldom specific enough to serve as identifying means. Unless some restorative, preventive, or orthodontic treatment is done that would provide a basis for identification, their dental chartings will have no distinguishable characteristics that might not be shared by many other individuals.

In view of the flouridation of public water supplies, which has reduced the amount of tooth decay in children, it is likely that in the future, even a lower percentage of children will have dental chartings that could be used for identification.

This is a serious problem, since according to Child Find, a national organization for finding and identifying missing children, between 20,000 and 50,000 children become missing each year under suspicious circumstances. Of these it is estimated that about 5000 are found and over 3000 murdered.

Although bite impressions of wax or other material are often made of a persons teeth, such impressions are used for indicating the location of the upper and lower teeth in relation to each other. Since they usually provide a record only of the occlusal surfaces of the teeth, and no information about the other tooth surfaces, such impressions generally do not give sufficient information for accurate identification, and to my knowledge, bite impressions have never been used for such purpose.

SUMMARY OF THE INVENTION

This invention relates to a method and an article for providing identification means, comprising taking an impression of the teeth of a person with a wax wafer of particular configuration which provides an impression giving the size and shape of each tooth from the occlusal surface to the gum line, and provides information on the tooth positions and jaw relationship, to provide maximum identifying information. The wafer can be used for taking an impression of a child's teeth either by a dentist, or by a parent or a school nurse.

The wax impression is then stored for use in case of need, in a suitable container, which preferably has means for receiving a security seal to indicate that the contents of the container have not been tampered with.

DESCRIPTION OF IHE ILLUSTRATED EMBODIMENT

Figure 1:
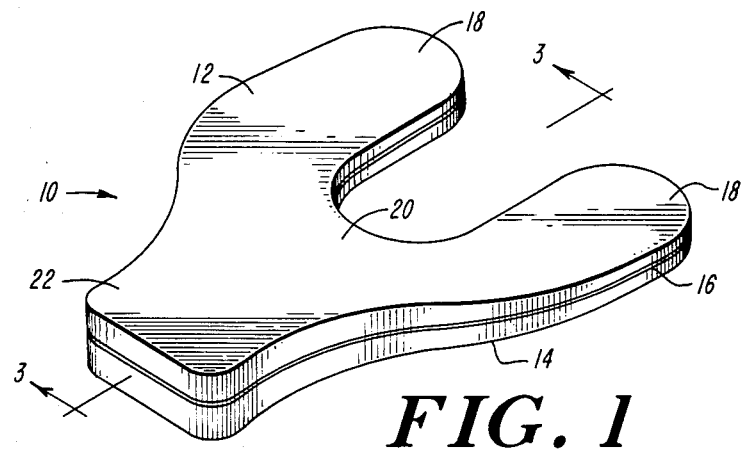
FIG. 1 is a perspective view of a wafer for making a dental impression for identification purposes embodying the features of the invention.
Figure 2:
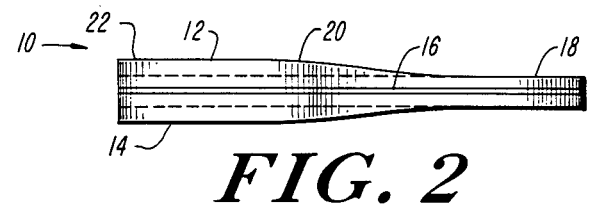
FIG. 2 is a view in side elevation of the wafer of FIG. 1.
Figure 3:
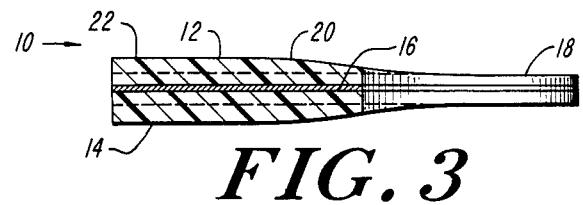
FIG. 3 is a view in section taken on line 3—3 of FIG. 1.
Figure 4:
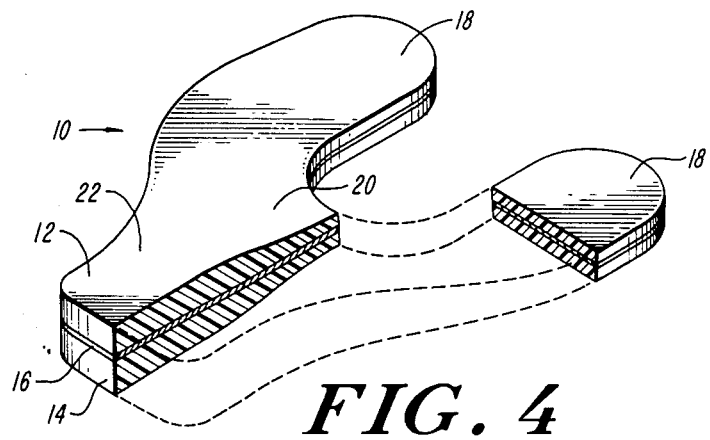
FIG. 4 is a view similar to FIG. 1, partly broken away.

Referring to FIGS. 1-4 of the drawings, there is illustrated a wafer 10 for taking the impression of human teeth, said wafer comprising upper and lower layers 12 and 14 respectively of wax of the type commonly used for such purpose, said layers being separated by a sheet of material 16 such as aluminum foil.

In a preferred embodiment of the wafer, it has a plan shape which is generally U-shaped with a pair of posterior segments or lobes 18 joined by an anterior segment 20, and a handle portion 22 extending from the portion 20.

The wafer is shaped to allow it to be inserted into a person's mouth so that the lobes 18 are positioned between the upper and lower molars, and the anterior portion is positioned between the front teeth, that is, the incisors and the canines.

For this purpose the upper and lower layers of each lobe have a thickness such that when the wafer is bitten by a person to form an impression, the layer can receive an impression of not only the biting surface down to the mesial marginal ridge, but also an impression of the inside and out side surfaces of the molars down to the gum line.

The upper and lower layers of the anterior portion 20 are thicker than the upper and lower layers of the posterior lobes, so that a complete impression, including the facial and lingual (front and back) surfaces of the incisors and canines are obtained.

Wafers formed of two layers of wax with an intervening layer of aluminum foil are known in the art, however such wafers are used to provide jaw location information, and are of uniform thickness, and impressions made with such wafers do not provide sufficient information about the shape of the individual teeth to reliably permit positive identification. Such wafer material is commonly formed as a sheet or continuous strip and the individual wafers are punched out of the sheet by a ribbon die.

One method of manufacture of a wafer as described herein is to utilize the above described wafer sheets as now manufactured with a uniform thickness, and superimpose onto said sheet other layers of wax to achieve the thickness desired. Another method of manufacture would be to provide a wafer sheet with a wax thickness on both sides which at least equal to the desired thickness of the connecting portion of the wafer 10, and then compression molding the wafer in suitable dies so that the desired thickness of each portion of the wafer is obtained.

In the illustrated embodiment the lobes 18 have rounded ends, with no wafer material between the lobes, since such a shape is easier to insert into a childs mouth, and is less threatening to a small child, than wafers which have continuous wafer material between the position of the biting surface of the rear teeth and square ends, which appear to be bigger and may therefore be more frightening to a small child. The absence of material between the lobes also helps to reduce gagging which sometimes occurs on insertion of a wafer into the mouth.

The projecting handle portion 22 provides a convenient means of handling the wafer during the impression process, particularly when the impression is taken by persons inexperienced in dental methods, such as a parent or a school nurse.

The wafer is used to take an impression of teeth in the usual manner, by first warming the wafer, such as in heated water, to a temperature which is hot to the touch but not scalding, inserting the wafer into the mouth far enough that the connecting portion 20 is below the front teeth, and insuring that the lobes 18 are below the upper rear teeth, and having the person whose impression is being taken bite firmly down onto the wafer as far as possible, so that an impression of all of the upper and lower teeth is obtained on the upper and lower wax layers 12 and 14 respectively.

The wafer may then be removed from the mouth by separating it gently from the teeth. Either just before or just after the impression is taken, the wafer is provided with identifying means, which should include the name, address, and age of the person making the impression. The identifying means may be provided by applying it to a suitable surface on the wafer, or by providing a tag, bearing the identifying information, attached to the wafer.

After the impression is taken and provided with suitable identification means, the wafer should be stored in a small container having closure means that includes a security seal, to discourage casual opening of the box, and to detect tampering.

Figure 5:
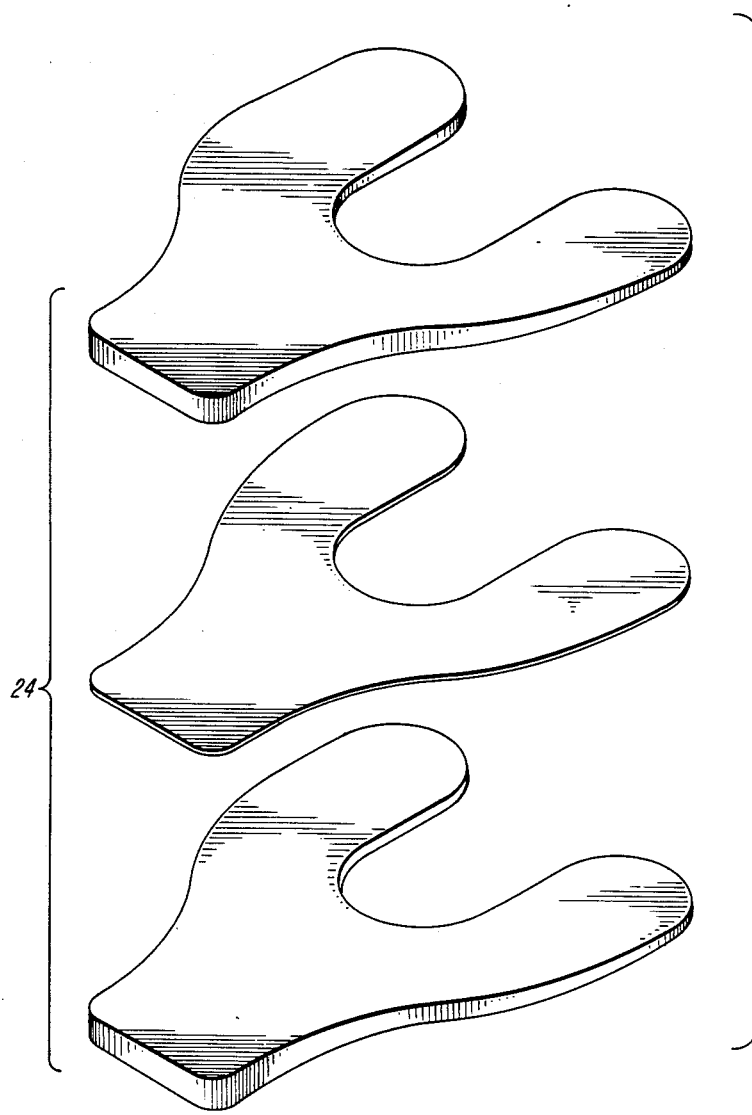
FIG. 5 is an exploded view of the components of a modified form of wafer.
Figure 6:
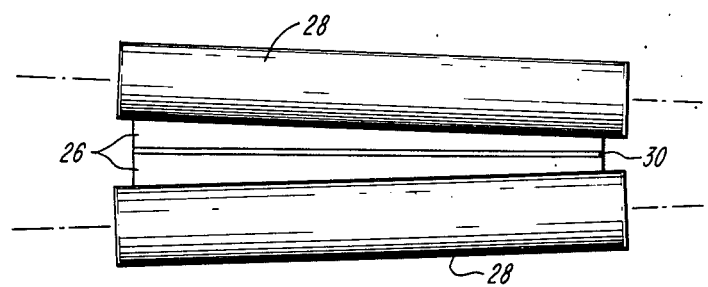
FIG. 6 is a view partly in section illustrating a method of manufacturing the wafer of FIG. 5.

Referring now to FIGS. 5-7 of the drawings, there is illustrated a modified form of wafer and a method of manufacture thereof. In this embodiment, a wafer 24, which has a plan shape substantially the same as that of the wafer of FIGS. 1-4, may be manufactured by rolling a strip 26 of wax between suitable rollers 28 which are not parallel, but are disposed at at a suitable angle to provide a desired thickness at the opposite edges of the strip.

Two of the strips 26 may then be superimposed with their thick and thin edges on the same side, with a layer of aluminum foil 30 between the strips, which are adhered to the foil layer by any suitable means.

The resulting strip assembly may then be cut by a ribbon die or other suitable means to form the wafer 24, which will have a uniform taper from the front to the rear, providing adequate thickness of the posterior lobes 32 for an impression of the primary and permanent molars substantially to the gum line, and a greater thickness at the anterior portion for an adequate impression of the incisors and canines.

In the case of a small child, the ideal procedure would be to take an impression on a yearly basis, although such procedure might not be diligently followed by most parents.

Therefore a recommended schedule would be to take a first impression of a child's teeth at about age 3, after all 20 primary teeth have erupted, a second impression at about age 6½-7, after the four mandibular (lower) incisors have erupted, a third impression at about age 7½-8 after the four maxillary (upper) incisors have erupted, and a fourth impression at about age 12-13 after all permanent teeth (excluding third molars) have erupted.

If dental treatment is provided after the time at which an impression is taken, and the treatment is of a type which will provide positive identification, then subsequent impressions may not be necessary.

Since certain changes obvious to one skilled in the art may be made in the above described embodiments of the invention without departing from the scope thereof, it is intended that all matter contained herein be interpreted in an illustrative and not a limiting sense.

I claim:

1. A wafer for taking a simultaneous impression of upper and lower teeth, comprising upper and lower layers of impressionable material separated by a layer of ductile material, said wafer having a pair of laterally spaced portions to receive the impression of the molars and being thick enough to record the shape of the molars from the biting surface substantially to the gum line, and a thicker anterior portion extending between the posterior portions and positioned to receive an impression of the front teeth from the biting edge substantially to the gum line.

2. A wafer as set out in claim 1 which is generally U-shaped in plan with the posterior portion being formed by a pair of spaced legs, the anterior portion connecting said spaced legs and being thicker than the legs.

3. A wafer as set out in claim 2 in which said legs have rounded ends.

4. A wafer for taking a simultaneous impression of a person's upper and lower teeth, comprising upper and lower layers of impressionable material with an intervening layer of ductile material capable of being easily and permanently deformable by biting, said wafer having a pair of separate legs and a connecting portion disposed in generally a U-shape that conforms to the position of teeth in a human mouth, the ends of the legs being rounded, and a handle extending from the connecting portion, in which the upper and lower layers of impressionable material of the connecting portion are thicker than the corresponding layers on the legs.

5. A wafer for taking a simultaneous impression of upper and lower teeth, comprising upper and lower layers of material suitable for taking such an impression separated by a layer of ductile material, in which the wafer has a posterior portion to receive an impression of molars and an anterior portion to receive an impression of canines and incisors, in which the wafer thickness increases from the rear of the posterior portion to the front of the anterior portion.

* * * * *